(12) United States Patent
Keast et al.

(10) Patent No.: US 8,517,955 B2
(45) Date of Patent: Aug. 27, 2013

(54) TISSUE SAMPLING DEVICES, SYSTEMS AND METHODS

(75) Inventors: Thomas M. Keast, Sunnyvale, CA (US); Aaron M. Weiss, San Francisco, CA (US); Eric J. Gwerder, Fremont, CA (US); Jeffrey Schwardt, Palo Alto, CA (US); Edmund J. Roschak, Mission Viejo, CA (US)

(73) Assignee: Broncus Medical Inc., Mountain View, CA (US)

( * ) Notice: Subject to any disclaimer, the term of this patent is extended or adjusted under 35 U.S.C. 154(b) by 425 days.

(21) Appl. No.: 12/776,978

(22) Filed: May 10, 2010

(65) Prior Publication Data

US 2010/0312141 A1    Dec. 9, 2010

Related U.S. Application Data

(60) Provisional application No. 61/176,859, filed on May 8, 2009, provisional application No. 61/229,226, filed on Jul. 28, 2009.

(51) Int. Cl.
*A61B 5/00*    (2006.01)

(52) U.S. Cl.
USPC .......................................................... 600/564

(58) Field of Classification Search
USPC .................................. 600/562–567; 606/172
See application file for complete search history.

(56) References Cited

U.S. PATENT DOCUMENTS

| | | | |
|---|---|---|---|
| 5,246,011 A * | 9/1993 | Caillouette | 600/566 |
| 6,749,576 B2 * | 6/2004 | Bauer | 600/567 |
| 7,481,775 B2 * | 1/2009 | Weikel et al. | 600/567 |
| 8,337,516 B2 * | 12/2012 | Escudero et al. | 606/159 |

* cited by examiner

*Primary Examiner* — Max Hindenburg
(74) *Attorney, Agent, or Firm* — Levine Bagade Han LLP

(57) ABSTRACT

Methods, devices, and systems are described herein that allow for improved sampling of tissue from remote sites in the body. A tissue sampling device comprises a handle allowing single hand operation. In one variation the tissue sampling device includes a blood vessel scanning means and tissue coring means to excise a histology sample from a target site free of blood vessels. The sampling device also includes an adjustable stop to control the depth of a needle penetration. The sampling device may be used through a working channel of a bronchoscope.

10 Claims, 12 Drawing Sheets

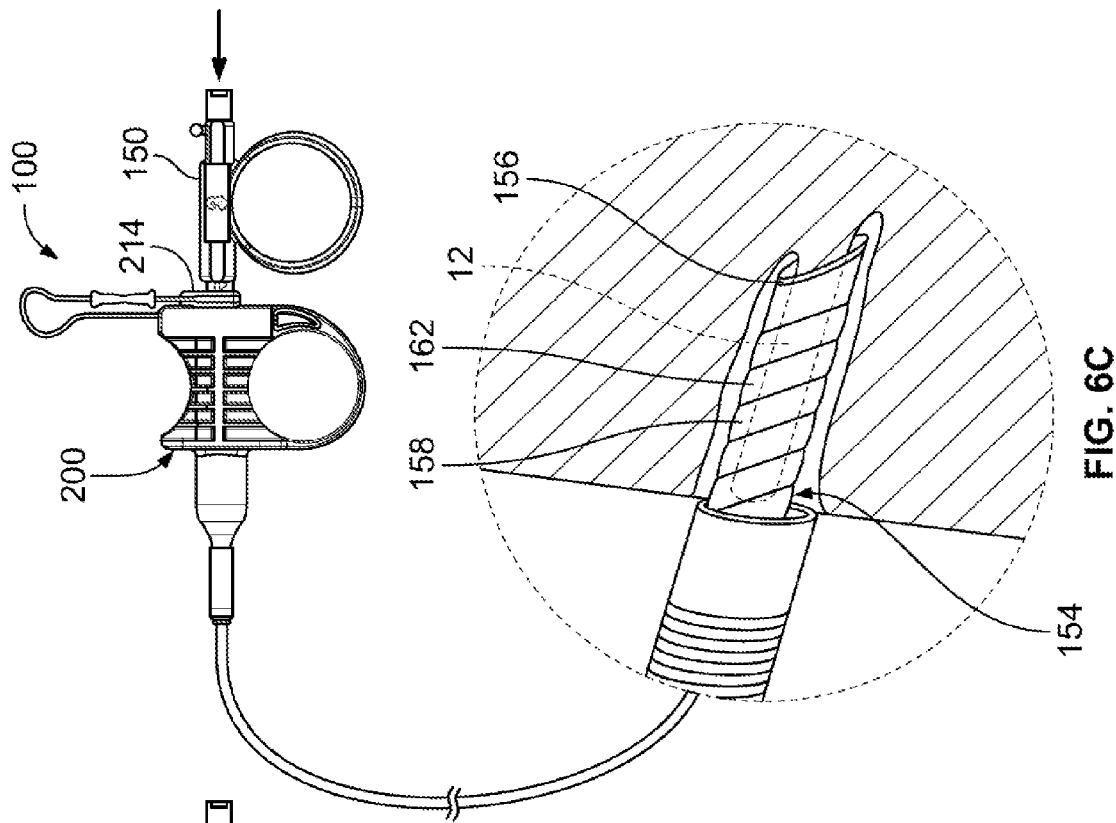
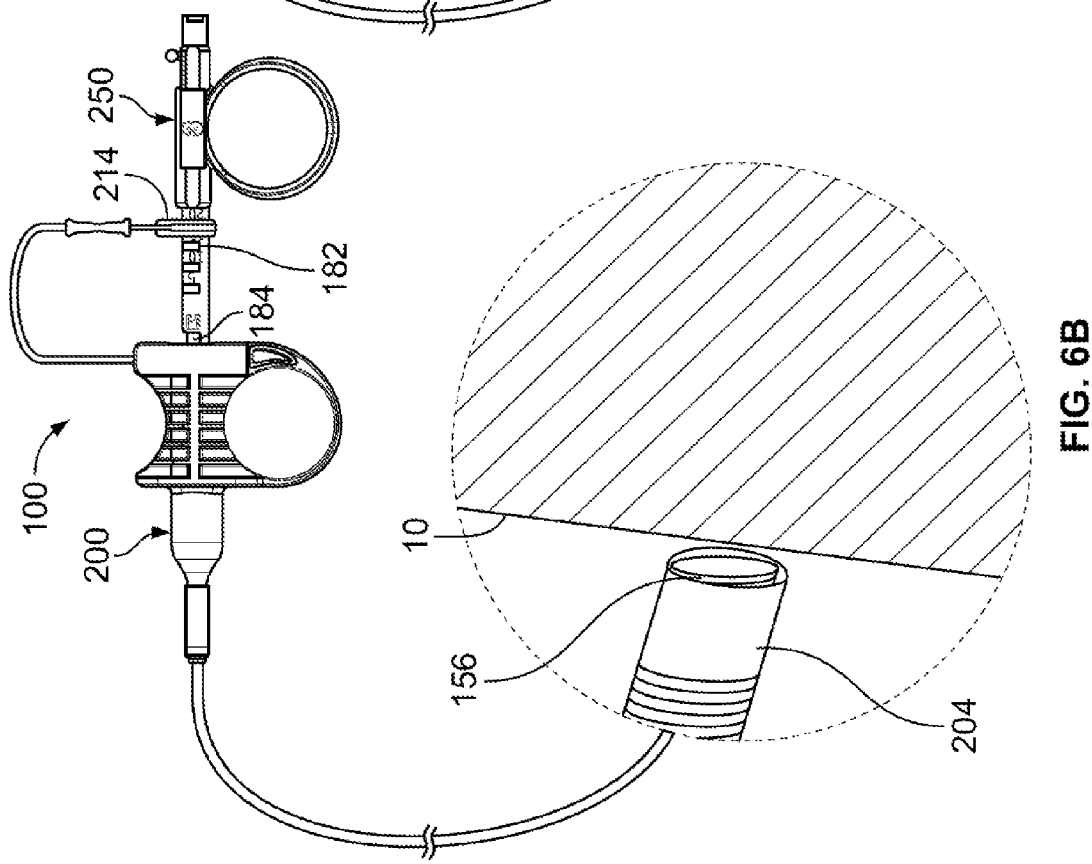

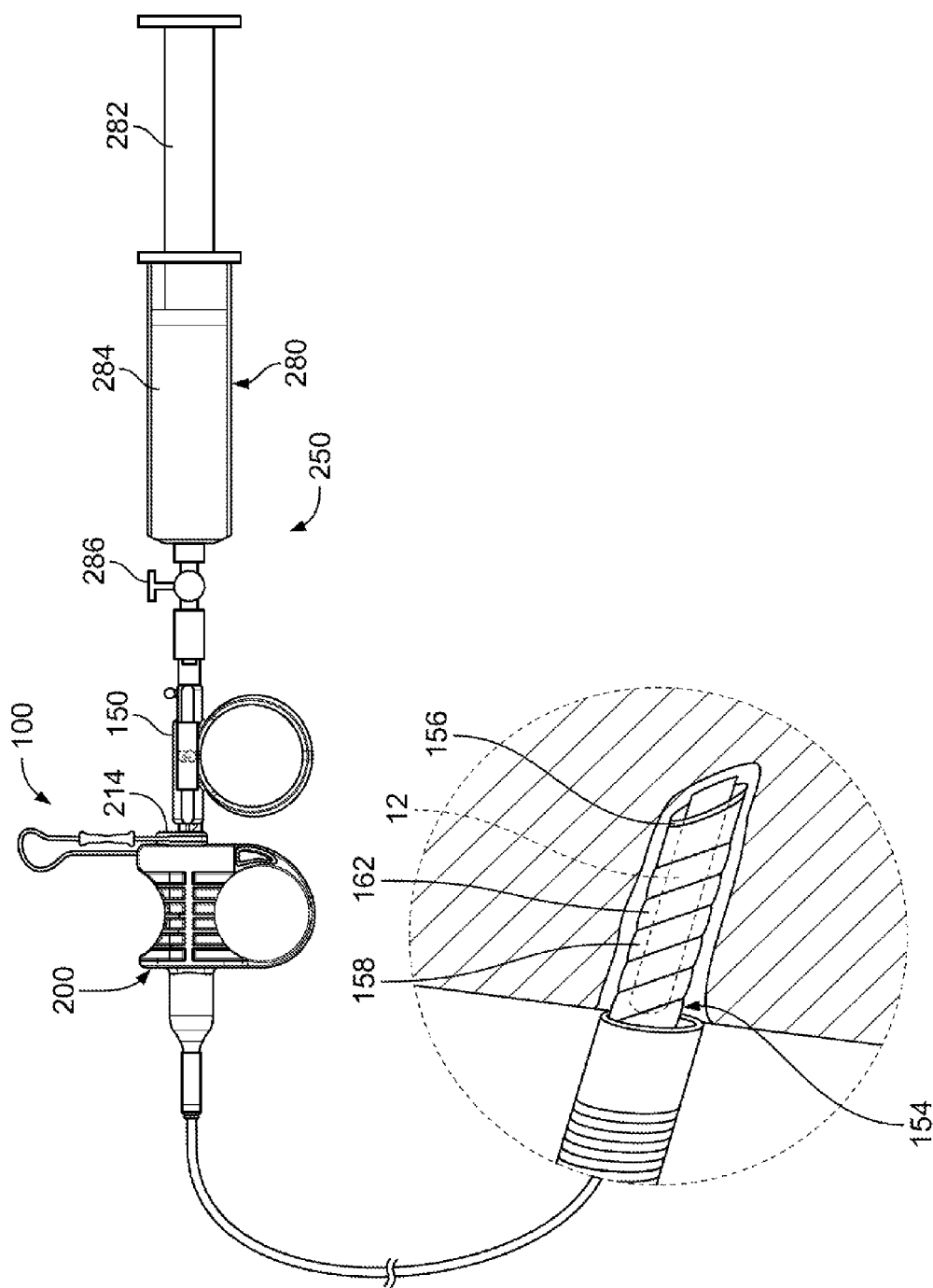

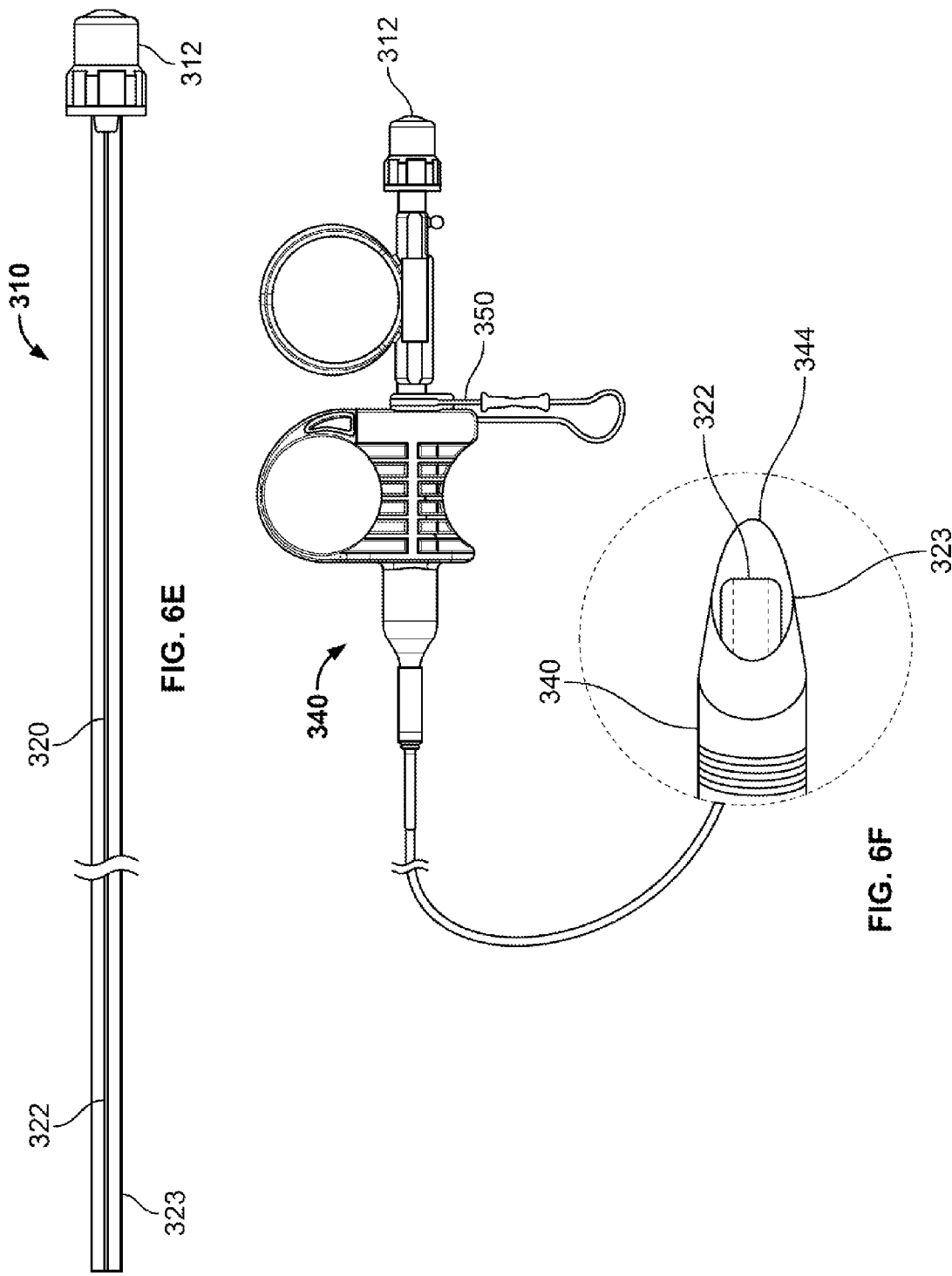

TISSUE SAMPLING DEVICES, SYSTEMS AND METHODS

CROSS REFERENCE TO RELATED APPLICATION

This application is a non-provisional of prior U.S. Provisional Application No. 61/176,859 filed May 8, 2009 and U.S. Provisional Application No. 61/229,226 filed Jul. 28, 2009, the entirety of both of which are incorporated by reference.

FIELD OF THE INVENTION

The present invention relates to tissue sampling devices and methods that allow sampling of tissue at remote regions in the body where the devices and methods provide improved safety features while also providing configurations that employ ease of use by a physician in a manner similar to a biopsy gun while using a less complex configuration.

BACKGROUND

Rapid advancements in medicine are increasingly providing physicians with opportunities to treat medical conditions at an earlier stage leading to an increase in positive outcomes for their patients. Advancements in the fields of pharmaceutical substances, biotechnology, medical procedures as well as medical devices often drive these advancements. However, such advancements are also leading to an increase in the need of a physician to obtain a portion of tissue from the body to properly diagnose or confirm the medical condition.

In those cases where the physician suspects cancer, the physician attempts to confirm the diagnosis using any number of procedures including non-invasive imaging or even physical palpation to inspect the suspected site. Next, the physician typically obtains a sample of tissue (via a biopsy procedure) to confirm the presence or absence of the disease. A physician can perform a biopsy procedure either using open surgical techniques or minimally invasive/percutaneous techniques. While an open biopsy allows the greatest amount of access to the site, there are also a considerable number of adverse consequences with open procedures. Aside from the cost and recuperation time for the patient, the procedure often must be performed on an already sick patient, who may incur additional side effect. In contrast, a minimally invasive or percutaneous procedure removes a core sample of the suspected tissue mass or lesion. Such procedures are performed with needle or coring type devices. The sample can be aspirated or ejected from the needle for proper evaluation.

Such minimally invasive biopsies can include fine needle aspiration (FNA), transbronchial needle aspiration (TBNA), or core biopsies. In a FNA biopsy, the physician obtains a group of cells for cytological examination.
However, such examination often only allows an examination on the cellular level and often only after the results are processed through a medical laboratory. In a core biopsy, the physician obtains a core sample of tissue for histological examination which may be done after the core tissue sample is frozen or put in a preserving substance (e.g., formalin, a paraffin material or other material that preserves the structure of the tissue). Although any number of biopsy procedures may be required depending on the suspected condition or disease, a core biopsy can be extremely useful and are frequently desired and if available chosen by physicians.

A basic biopsy technique requires considerable manual dexterity and coordination. Such procedures often require the use of both hands, to advance a stylet while maintaining the position of a cannula and then to maintain the position of the stylet while advancing the cannula. Problems can occur if the physician advances the cannula too slow. Slow advancement often results in a poor cutting action and allows the surrounding tissue an opportunity to collapse, or displace without efficient cutting of the cored tissue. Additional complications can occur if the tissue to be sampled contains areas of higher density than that of surrounding tissue. Such discrepancies can occur with calcification commonly associated with certain types of cancerous growths. Slow device advancement may result in the device deflecting against dense tissue. This causes the trajectory of the cannula/stylet structure to move around the dense area and into the more compliant surrounding tissue, potentially missing the intended target.

Many core samples are obtained using a biopsy gun. The term "biopsy gun" often refers to a tissue sampling or coring device designed for single-handed manipulation by a physician. Often, the shape of the "biopsy gun" is adapted to fit within a hand of a medical practitioner via a pistol-like or syringe-like grip, complete with a triggering mechanism that relies upon a spring mechanism to drive the cannula to sever the tissue core. However, such devices are relatively complex design resulting in a relatively inflexible device and are typically intended for accessing areas such that are not remotely located within the body (such as the skin surface, breast tissue, etc.).

There is also a compelling need and desire to minimize the burden on the patient by obtaining such a core sample of tissue from deep within the body through minimally invasive means. Doing so can significantly decrease the cost of the procedure as well as the recuperation time of the patient. Moreover; devices and methods that allow less invasive means of obtaining tissue samples from deep within the body can also decrease any reluctance to obtain the sample of tissue, thereby increasing the frequency of occurrence for deep core biopsy procedures.

Many times cancerous tumors, pre-malignant conditions and other diseases or disorders occur within organs or at sites remotely within the body. In such cases, obtaining a tissue sample from the suspected diseased site presents a number of challenges. First, a sample must be obtained without causing inadvertent damage to the patient. Secondly, the physician must obtain a sufficient size of a tissue sample in order to determine the nature or state of the disease. Third, the target tissue might be located within tortuous anatomy of the body and adjacent to other tissue structures or organs. Clearly, any number of additional concerns exists when trying to obtain a desirable tissue sample.

A number of challenges arise when performing procedures through an endoscope, bronchoscope, or other such device. For example, there is a risk that the biopsy device might disrupt structures beneath a tissue surface (such as blood vessels), where the disruption then causes significant complications or effects that may prolong the procedure.

One such area is within the airways of the lungs where puncturing of a blood vessel beneath the airway surface can result in significant bleeding. In cases where a scope type device is used, the bleeding obstructs the ability of the medical practitioner to visualize the damaged area resulting in an escalation of complications. In some cases, a patient's chest must be opened to stem the bleeding.

Scanning for blood vessels underneath the airway wall mitigates the above described problem but is not without its own challenges. For example, because airway or other lung tissue moves due to tidal motion of the lungs (as a result of the mechanics of breathing), it is difficult to visually identify the area that was scanned for blood vessels unless the scanning device remains relatively stationary against the tissue. Moreover, the difficulty increases when considering that the procedure takes place through the camera of a bronchoscope or endoscope.

Aside from the risk to the patient, once the medical practitioner punctures a blood vessel, that practitioner is understandably hesitant or risk adverse when performing future procedures. As a result, while the benefit of these procedures is well known, the risks of complications may reduce the overall success of the procedure.

The devices, systems, and methods described herein allow for obtaining a core sample of tissue much like that obtained with a biopsy gun, but allow for obtaining the sample of tissue using a minimally invasive approach to access remote areas of the body. For example, such areas include but are not limited to the lungs, the liver, the digestive tract, organs within the thoracic cavity, etc. Furthermore, the devices, systems, and methods allow for improved safety when obtaining such biopsy samples.

BRIEF SUMMARY OF THE INVENTION

The problems noted above are solved by the methods and devices described herein. Such methods and devices include a core tissue sampling system and use thereof for navigating to remote sites within the body to obtain a core sample of tissue from a target site. The system includes safety features to minimize unintended injury to the patient or to the target site when excising tissue from remote sites within the body.

In one variation, the tissue sampling device is configured to have multiple set penetration depths. Such a device can include a sheath being flexible to advance through tortuous anatomy; a shaft extending in the sheath, where the shaft and sheath are moveable relative to each other; a coring tip located at a distal end of the shaft, the coring tip having a tissue penetrating distal end and a cavity to retain a tissue sample; a handle assembly comprising a sheath hub and a coring hub moveably coupled thereto, the sheath hub located on the sheath and the coring hub located on the shaft, where the sheath hub and coring hub each include a grip surface located on the respective hubs to allow for a single handed movement of the sheath hub relative to the coring hub for moving the sheath relative to the shaft, where a length of the shaft and coring hub relative to a length of the sheath and the sheath hub is selected such that when the sheath hub is spaced a maximum distance from the coring hub, the coring tip is located within the sheath and when the sheath hub is spaced a minimum distance from the coring hub, the coring tip advances from the sheath; and the coring hub further comprising at least a plurality of recesses each configured to removably nest a stop member, the plurality of recess being located along a length of the coring hub, such that when the stop member is in one of the recesses, the stop member limits an advancement distance that the coring tip advances from the sheath.

Variations of the tissue sampling device can include any number of distance indicators to relay information to the physician as to the depth of penetration corresponding with the recess on the device or position of the stop on the device.

In order to access remote regions of the body, the devices described herein can be flexible while maintaining sufficient column strength to penetrate the tissue when actuated over a relatively long distance. Accordingly, the sheath and/or shaft of the coring device can include any number of reinforcing members located on or in the sheath/shaft. In addition, the sheath/shaft can have varying degrees of flexibility along a length thereof.

The systems described herein can also employ a sensing device though the coring device to check the target region for blood vessels or other structures. Such devices can include a Doppler catheter that determines the presence or absence of a blood vessel. In order for the Doppler catheter to ensure that the intended trajectory of the core device is free from blood vessels, the Doppler can be designed to be forward firing or to produce a narrow transmission cone. In this way, the Doppler catheter will scan tissue directly in the path of the device.

The devices described herein can employ any number of positive pressure, vacuum or aspirating sources and also can further include one or more fittings on a proximal end of the device, where the fitting is adapted to form a fluid seal with the positive pressure, vacuum or aspirating source.

In another variation of the device, a tissue sampling system can be configured to have at least one set penetration depth. Such a device include a sheath being flexible to navigate tortuous anatomy; a shaft extending in the sheath, where the shaft and sheath are moveable relative to each other, where the shaft has a sufficient flexibility to navigate tortuous anatomy; a coring tip located at a distal end of the shaft, the coring tip having a sharp edge or tip to excise a tissue sample and a cavity to temporarily retain the tissue sample; a device handle comprising a sheath handle and a shaft handle moveably coupled thereto, the sheath handle affixed to a proximal end of the sheath and the shaft handle affixed to a proximal end of the shaft, where the sheath handle and shaft handle each include a grip surface situated to allow for single handed movement of the shaft handle relative to the sheath handle to move the shaft relative to the sheath, where when the sheath handle is spaced a maximum distance from the shaft handle, the coring tip is located within the sheath and when the sheath handle is spaced a minimum distance from the shaft handle, the coring tip advances from the sheath to the defined penetration depth; and a Doppler catheter having a Doppler sensor located at a distal end of a catheter shaft, the Doppler is an optional accessory device, which is slidable though the shaft.

The present disclosure also includes methods and procedures for obtaining a tissue sample from a lung. In one variation, such method includes advancing a tissue sampling catheter into an airway of the lung, where the tissue sampling catheter comprises a sheath having a shaft extending therethrough, the shaft having a coring tip comprising a tissue penetrating distal end to penetrate tissue and a cavity to excise the tissue sample, where the coring tip is retracted within the sheath when the tissue sampling catheter enters the airway of the lung; positioning a distal end of the sheath adjacent to a site in the airway; advancing a Doppler catheter through the tissue sampling catheter such that a tip of the Doppler catheter exits through the coring tip; scanning the site for determining a presence or absence of a blood vessel using the Doppler catheter; retracting the Doppler catheter from the coring tip; advancing the coring tip from the sheath by thrusting the shaft handle; and penetrating tissue with the coring tip such that the sample of tissue is captured and retained or located within the cavity of the coring tip; aspirating the sample.

In one variation, the method includes advancing the coring tip from the sheath by a pre-determined distance that is set using a positionable stop located on the coring hub, where the adjustable or removable stop limits the pre-determined distance that the coring tip advances from the sheath.

In an additional variation, the method includes actuating a handle to drive the coring tip into tissue, where the handle comprises a sheath hub and a coring hub moveably coupled thereto, where the sheath hub and coring hub each include a digit grip surface located on the respective hubs to allow for single handed movement of the sheath hub relative to the coring hub by the pre-determined distance for moving the shaft relative to the sheath.

In another variation a method includes obtaining a tissue sample from an airway in a lung by pre-selecting a maximum depth of the needle penetration which corresponds to the depth of the sample in tissue. For example, such a method can include advancing a tissue sampling catheter into an airway of the lung, where the tissue sampling catheter comprises a sheath having a shaft extending therethrough, the shaft having a coring tip comprising a tissue penetrating distal end to penetrate tissue and a cavity to excise the tissue sample, where the coring tip is retracted within the sheath when the tissue sampling catheter enters the airway of the lung; positioning a distal end of the sheath adjacent to a site in the airway; setting an adjustable stop on a handle of the tissue sampling catheter, where a location of the adjustable stop on the handle determines a pre-determined distance that the coring tip extends from the sheath, where the pre-determined distance corresponds to the maximum depth; actuating the handle to extend the coring tip from the sheath by the pre-determined distance; and penetrating tissue with the coring tip such that the sample of tissue is located within the cavity of the coring tip.

In another variation, aspiration is applied with an aspiration means, namely a vacuum or syringe, to the needle lumen. The sample is sucked into the cavity and held in place.

BRIEF DESCRIPTION OF THE SEVERAL VIEWS OF THE DRAWINGS

FIGS. 6B to 6D illustrate a variation of the tissue sampling device retrieving a core sample of tissue from the body.

FIGS. 6E to 6F illustrate a variation of the tissue sampling device comprising a stylet.

DETAILED DESCRIPTION OF THE INVENTION

Figure 1:
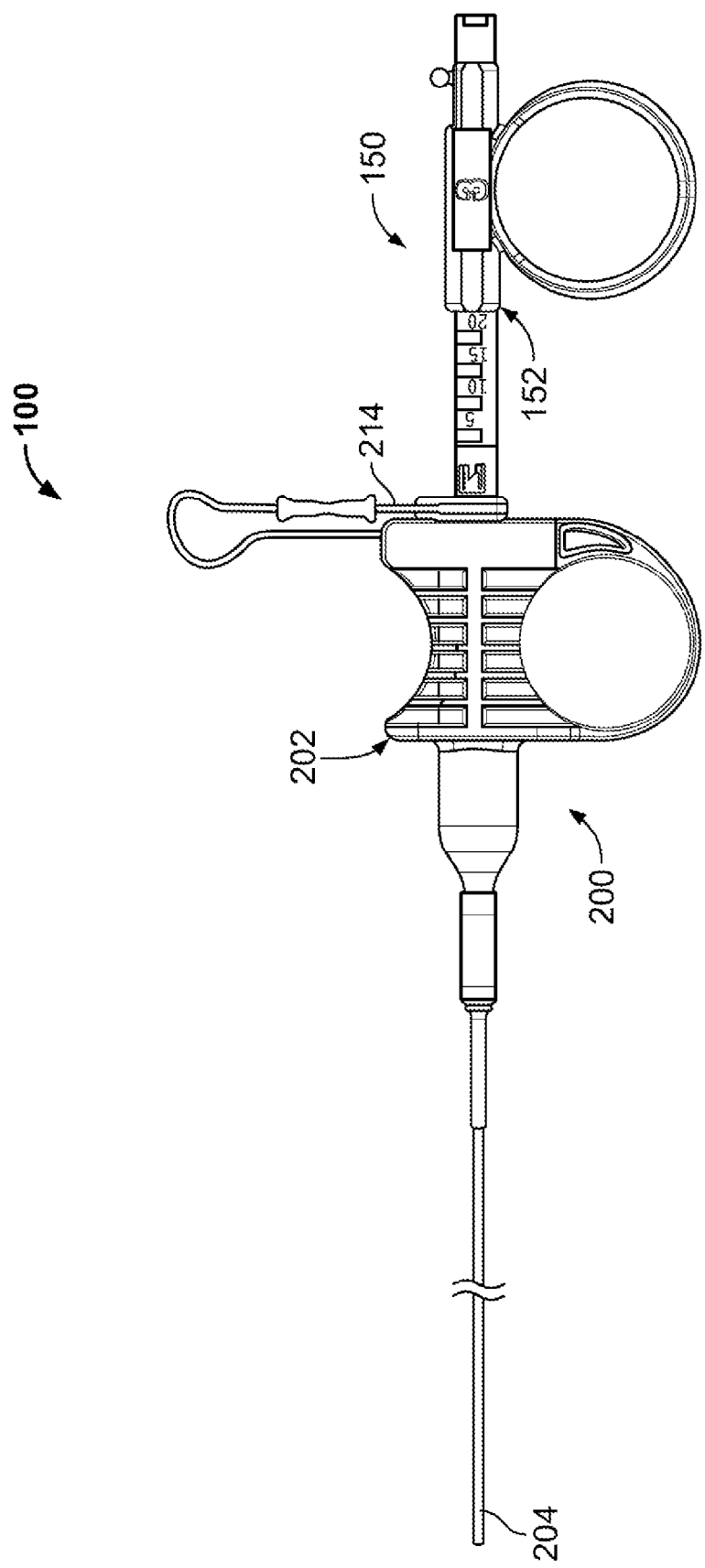
FIG. 1 illustrates an example of a tissue sampling device.

FIG. 1 illustrates an example of a tissue sampling device 100 having a coring device 150 slidably coupled through a sheath device 200. The coring device 150 includes a coring handle 152 (also referred to as a coring hub) affixed to a shaft (not shown in FIG. 1), where the shaft extends through the sheath device 200. The sheath device 200 includes a sheath handle 202 (also referred to as a sheath hub) affixed to the sheath 204 (typically at a proximal end). The coring handle 152 and the sheath handle 202 are slidably coupled to form a handle assembly of the tissue sampling device 100. In some variations, the coring handle 152 is keyed or otherwise configured so the coring device 150 cannot rotate relative to the sheath 200 or sheath handle 202. As is discussed below, the features of the coring handle 152 and sheath handle 202 provide an advantage when a user actuates the handle to drive the coring device 150 into tissue for capturing a sample of tissue while allowing for controlling the depth of penetration of the coring device 150. Part of the mechanical advantage is that the use of the two handles to increase the velocity and or force at which the coring device contacts/enters tissue. The device 100 also includes an adjustable stop 214 for limiting advancement of the coring device 150 and therefore controls the depth of penetration of the coring device.

This mechanical advantage allows the device 100 to function similar to that of a biopsy gun using the biomechanics of the user's hand. This advantage allows the user to drive the coring device into tissue at a velocity that is greater than that of conventional devices that rely on hand-thrust catheter/sheath advancement to drive a cutting device. The tissue sampling device can also be deployed using a hand-thrust to drive the coring device. The devices described herein also allow for thrusting the coring device through a low fiction sheath as opposed to thrusting a needle/catheter through a high friction bronchoscope/endoscope seal. Moreover, the ability to control or adjust the deployment length of the coring device 150 provides an added measure of safety when performing a biopsy. For example, limiting the stroke of the coring device reduces the possibility that the coring device causes collateral damage to tissue or organs adjacent to the target site. For example, in the case of a tumor that is adjacent to another organ, limiting the stroke length can prevent the core device from travelling through the tumor and into the adjacent organ. In the case where the device is used in the lungs, limiting the stroke length of the core device also reduces the chance that the device will breach the lungs or pleural membrane. This also reduces the chance to inadvertently puncture blood vessels distal to the target tissue.

Figure 2A:
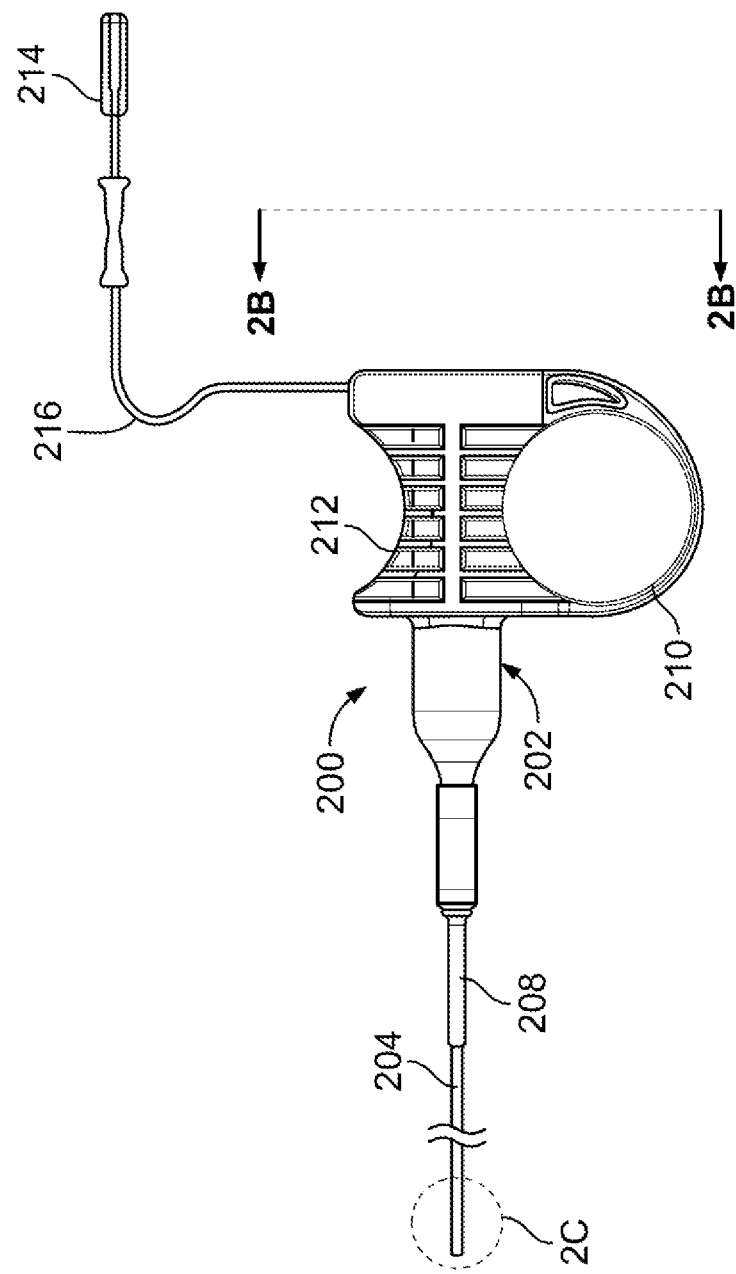
FIGS. 2A and 2B illustrate a side and back view of a sheath device.
Figure 2B:
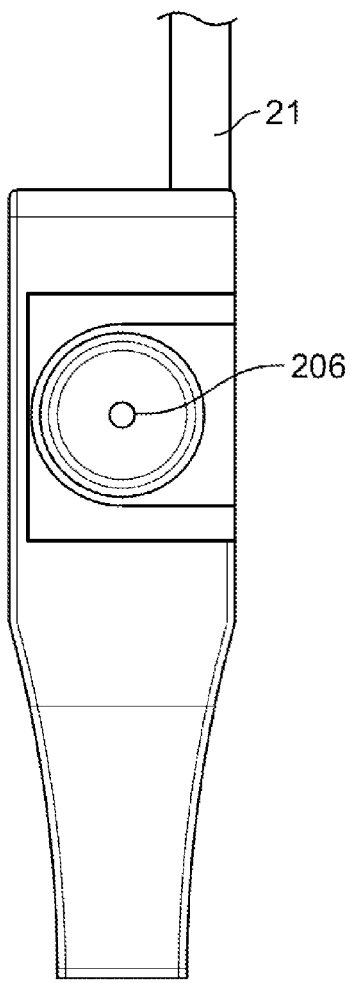

FIG. 2A illustrates an example of a sheath device 200 for use with a variation of a tissue sampling according to the present invention. As shown, the sheath device 200 includes a sheath handle 202 affixed or otherwise coupled to a sheath 204. The sheath handle 202 and sheath 204 include a sheath lumen 206 extending therethrough (as shown in FIG. 2B, which shows a view of the handle 202 taken along the line 2B-2B of FIG. 2A). The sheath lumen 206 allows for insertion of the coring device to the target site in tissue. As shown, the opening of the sheath lumen 206 can be tapered or stepped to ease loading of the core device into the sheath handle 202.

The sheath 204 can include one or more areas of increased strength to provide a stress relief or sleeve 208 to prevent kinking of the sheath 204 adjacent to the sheath handle 202. FIG. 2A also shows the sheath handle 202 including one or more grip surfaces 210 212. The grip surfaces 210 212 allow a user to manipulate the sheath hub 202 with one or more fingers/digits. For example, in the illustrated variation, grip surface 210 comprises a ring while grip surface 212 comprises a concave depression in the sheath hub 202. Additional variations of the sheath hub 202 include both grip surfaces comprising a ring or concave depression. Moreover, alternate variations of grip surfaces include any type of protrusion, contoured/frictional surface that improves the ability of a user to manipulate the sheath hub 202 especially when excising the tissue core as described below. FIG. 2A also illustrates the sheath hub 202 including an adjustable/removable stop or locking member 214 for the coring device. Although the variation shown in FIG. 2A shows the adjustable stop member 214 as being attached to the sheath handle 202 via a flexible extension 216, additional variations of the device can include one or more stop members 214 that are separate from the sheath handle 202 or separate from the tissue sampling device 100 entirely.

Figure 2C:
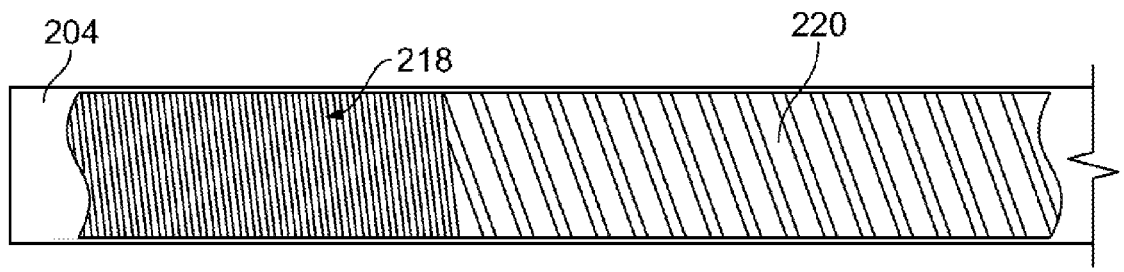
FIG. 2C illustrates a partial cross section of a distal end of a sheath of a sheath device.

FIG. 2C illustrates a partial cross section of a distal end of the sheath 204. As noted herein, the sheath 204 comprises a sufficient flexibility so that the user can navigate the device to remote target sites or tortuous anatomy within the body. Accordingly, the sheath can have varying regions of flexibility (e.g., very flexible at a distal portion and relatively stiffer at a proximal portion). In additional variations, the sheath 204 can be reinforced with a braid and/or coil to mitigate the coring device from penetrating the sheath. Sheath penetration may result in endoscopy equipment damage or an unsafe condition for the user or patient. In the illustrated variation, the sheath 204 includes a coil 218 located at or near a distal end. The sheath 204 can also optionally include a second reinforcing coil or braid 220 along some or all of the proximal section. In any case, the interior lumen or channel of the sheath can be designed as a low friction surface to reduce the drag on the core device as it advances through the sheath 204. This reduced frictional interface can allow faster actuation of the core device when advanced through the sheath 204. In addition, the sheath 204 can include any number of features commonly associated with catheters and sheaths (e.g., radiopaque markers, depth measurement indicators, etc.).

Figure 2D:
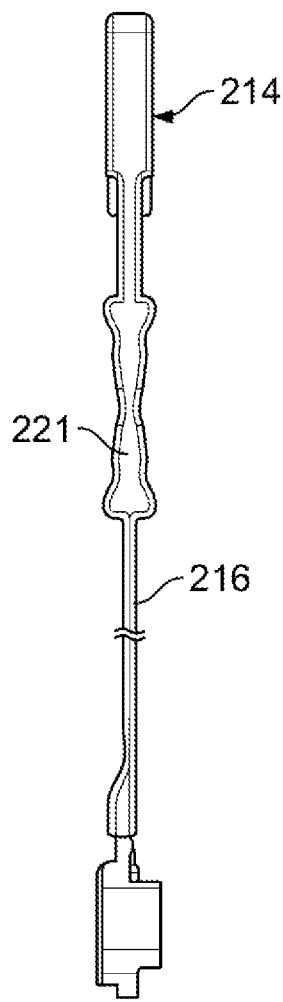
FIGS. 2D and 2E illustrate side and front views of a removable or adjustable stop that engages a coring device.
Figure 2E:
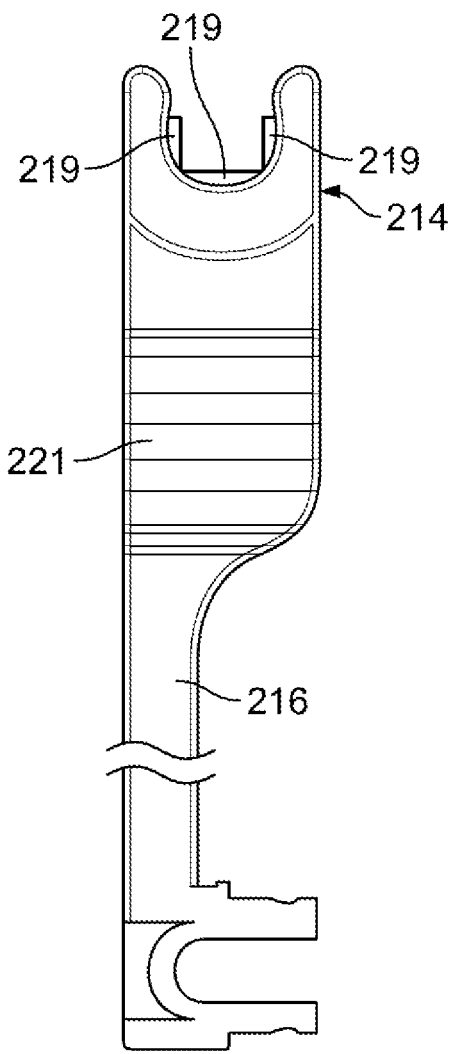

FIGS. 2D and 2E show respective side and front views of a variation of an adjustable stop member 214 for use with the devices described herein. As shown the stop member 214 can include a flexible extension or tether like member 216 so that it can be affixed to a sheath handle. As discussed below, the stop member 214 includes a section that couples to the core device to limit advancement of a tip device. In this manner, the user can limit the depth of penetration of the core device within tissue. Naturally, this feature allows the user to limit the depth of penetration which may impact the axial length of the core sample being excised. In a basic variation, the stop member 214 can simply couple to the core device via a friction fit. However, the illustrated variation shows a stop member 214 having a plurality of keys 219 that removably nest with mating pockets or keyways on a core device.

Figure 3A:
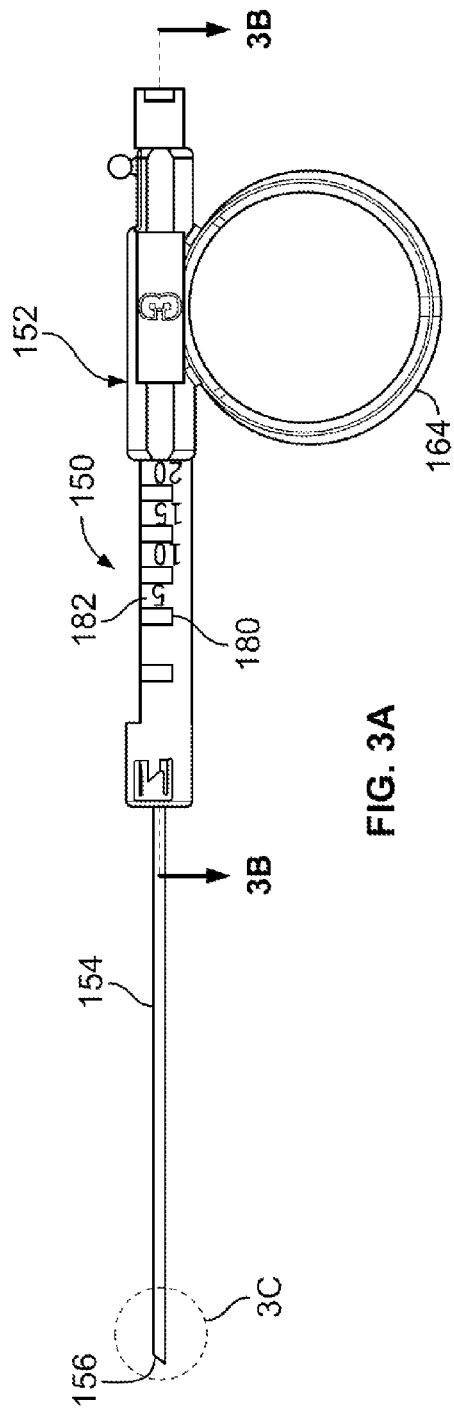
FIG. 3A shows a variation of a coring device.

FIG. 3A illustrates a variation of a coring device 150 similar to that shown in FIG. 1. In this variation, the coring device 150 includes a shaft 154 having a coring tip 156 located at a distal end of the shaft 154. The coring device 150 also includes a coring handle or coring hub 152 affixed to the shaft 154. In this variation, the coring handle 152 includes a grip 164 similar to that shown on the sheath handle 202 of FIG. 2A. Again, the finger grip 164 is not limited to the ring-type structure shown. Instead, any number of surfaces can be substituted in place of the ring. In any case, the grip 164 should allow a user of the device to use a single hand to produce a forceful thrust so that the coring tip can penetrate and excise tissue. In addition, the lumen 162 can have any number of tapered or conical sections.

FIG. 3A also shows a variation of the coring device 150 that includes a plurality of recesses, pockets or keyways 180 which receive the adjustable stop (e.g., as shown in FIGS. 2D and 2E). The recesses 180 can be located along a length of the coring handle 152, such that when the stop member is in one of the recesses, the stop member limits an advancement distance that the coring tip advances from the sheath. Therefore, a user of the device 100 can set the adjustable stop member in a desired location to control a length that the core tip 156 extends from the sheath. Such a feature limits the penetration depth of the coring device 150 where the combination of the coring device 150 and sheath device 200 provides a tissue sampling device having multiple set penetration depths.

Figure 3B:
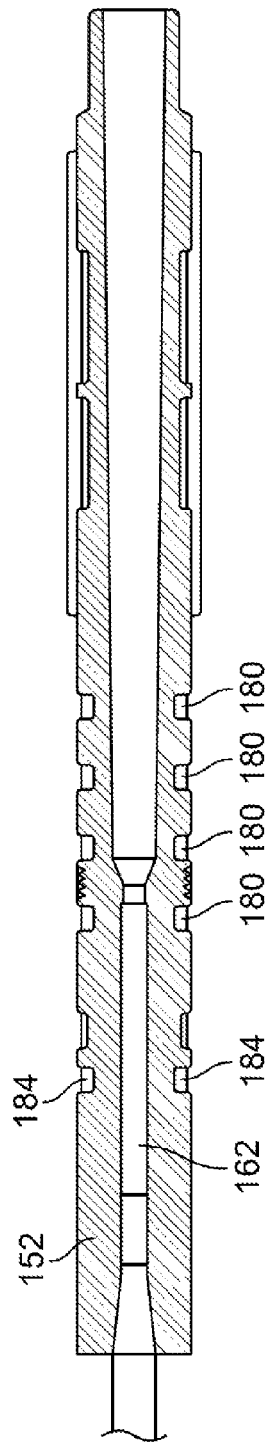
FIG. 3B is a cross sectional view of a coring handle of the coring device of FIG. 3A.

FIG. 3B is a partial cross sectional view of the coring device 150 of FIG. 3A. As shown, the recesses 180 are arranged along a length of the coring handle 152. The coring handle 152 includes a left-most recess 184 to keep the coring tip 156 recessed within the sheath to prevent accidental damage to the user or equipment caused by the coring tip 156. The coring handle 152 can include any additional stop surfaces to prevent removal of the coring handle 152 from the sheath handle. Accordingly, in some variations, when the adjustable stop is located in the left-most recess 184, the coring device 150 will be locked into place because the coring handle 152 or shaft 154 prevents further proximal movement of the coring device. (i.e., the coring device is prevented from proximal movement by the coring handle and prevented from moving in a distal direction because of the adjustable stop.)

FIG. 3B also shows an example of the plurality of recesses 180 being spaced along the coring handle 152 so as to provide incremental positions for the adjustable stop member. As noted above, this feature allows the user to control the depth of penetration of the coring device 150 into tissue. In addition, the coring handle 152 can optionally be constructed with depth indicators 182 that correlate the position of the recess 180 with the length of extension of the coring tip 156 from the sheath. Although four positions are shown, any number of positions can be employed. FIG. 3B also shows the tapered lumen from the proximal end to the distal end. The tapered section allows for the advancement of accessories through the coring handle and guides said accessories into the lumen of the shaft.

Figure 3C:
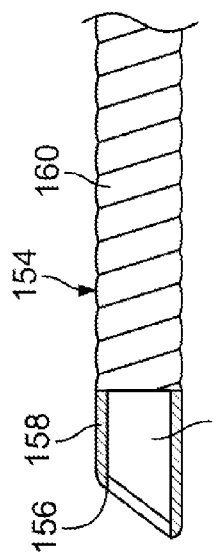
FIG. 3C shows a partial cross sectional view of a coring tip and shaft of the coring device of FIG. 3A.

FIG. 3C shows a partial sectional view of the coring tip 156 located at a distal end of the shaft 154. In the illustrated variation, the shaft 154 comprises a wound ribbon or coil 160. Typically, the wound ribbon or coil 160 will be sealed to permit aspiration through the shaft 154. This ribbon/coil 160 increases the flexibility of the shaft 154 as well as reduces the friction between the shaft 154 and the interior of the sheath. The ribbon/coil 160 can be affixed to a tube or cannula 158. The cannula 158 can be selected to have a relatively short length (e.g., in one variation the length of the cannula was 5 mm, however, the length can be chosen to be smaller or larger depending upon the particular application). However, the lumen 162 of the cannula 158 can be continuous through the ribbon/coil 160. As a result, a relatively long core sample of tissue can be obtained even though the core tip comprises a short length of cannula 158. As noted above, the core sample length shall be a function of the position of the adjustable stop. In certain variations, the core tip 156 comprises a beveled tip that is sharpened about the perimeter of the cannula 158.

Figure 4A:
FIGS. 4A to 4J illustrate a number of variations of coring and needle tips for use with the devices described herein.
Figure 4B:
Figure 4C:
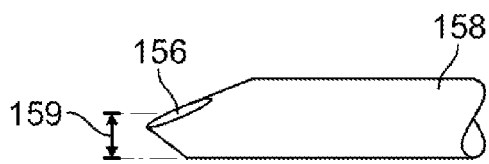
Figure 4D:
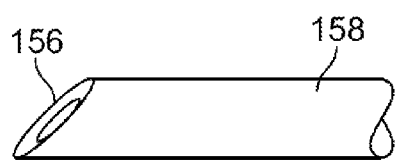
Figure 4E:
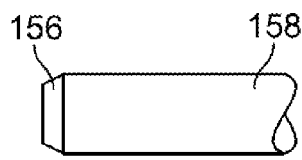
Figure 4F:
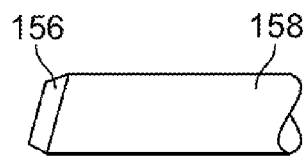
Figure 4G:
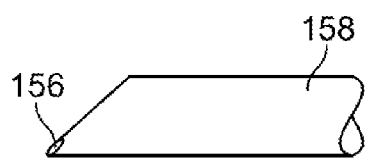
Figure 4H:
Figure 4I:
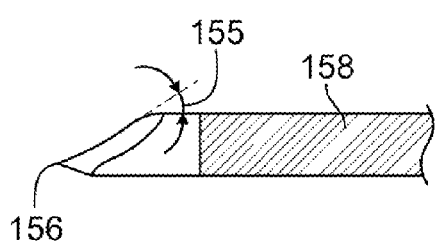

FIGS. 4A to 4J illustrate a partial list of examples of cannula 158 that can be used with the coring device 150 as described herein. For example, the cannula 158 can comprise a coring tip 156 with a long or short bevel tip (FIGS. 4A and 4B respectively). The coring tip 156 can comprise an offset 159 V-point (FIG. 4C). The coring tip 156 can comprise a J-point (FIG. 4D). The coring tip 156 can be a straight conical or angled conical point FIG. 4E or 4F. The tip 156 can comprise a 45 degree needle point FIG. 4G or even a trocar point FIG. 4H (the latter being used when not obtaining a coring sample). FIG. 4I illustrates an angled tip of a cannula 158.

Figure 4J:
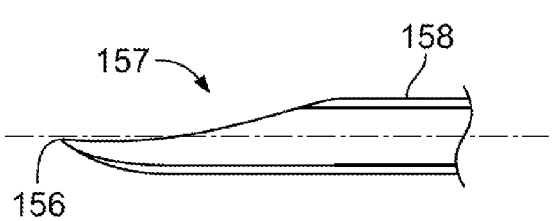

FIG. 4J illustrates a curved or beveled tip 156 at an end of a cannula 158. This latter tip 156 is similar to that of a lancet or septum penetrating needle. The curved tip 156 angles towards a centerline 157 of the cannula 158. Variations of the device include a curved tip that does not curve to the centerline or curves past the centerline. The curved tip reduces the chance that the coring tip 156 interferes or damages a wall of the sheath, and subsequently the bronchoscope or endoscope as the physician advances the needle.

The cannulae 158 described herein can be constructed of various materials commonly used in similar medical applications including, but not limited to stainless steel, Nitinol, metal alloy, etc.

Figure 5A:
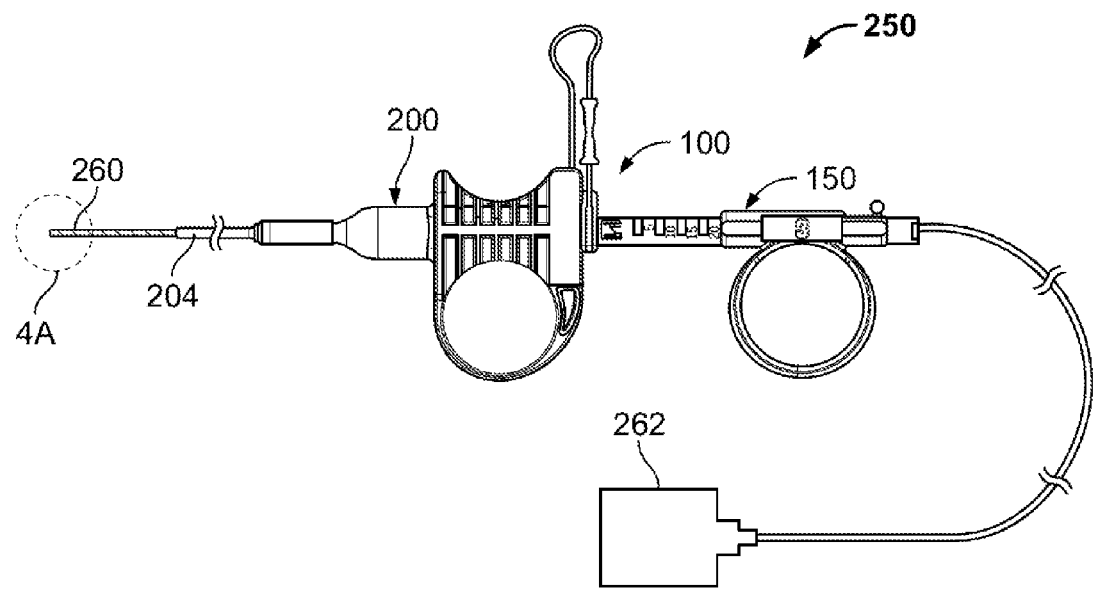
FIG. 5A illustrates a tissue sampling system including a tissue sampling device and a Doppler catheter with a Doppler processing unit.

FIG. 5A illustrates a variation of a tissue sampling device 100 when used as part of a tissue sampling system 250. In this variation, the tissue sampling system 250 includes a variation of a coring device 150 extending through a sheath device 200 both as described above. The system further allows for any number of medical devices to be delivered therethrough. In one example, a Doppler catheter 260 can be delivered through the coring device 150. However, any number of devices can be delivered through the tissue sampling device 100. For example, the tissue sampling device 100 can be used to deliver any number of devices that might be necessary or useful to scan or observe the area of tissue from which a core sample is desired. Such devices include, but are not limited to: a temperature measuring device, an optical fiber, an aspiration catheter, cautery probes for cauterizing bleeders, argon plasma probes for surface ablation, cryotherapy catheters for ablation or sampling, cytology brushes for parenchymal brushings or other brushing after penetration, cautery snares for excision of nodes, guide wires, wires for placing electrical leads for various medical devices, stylets/trocars, biopsy forceps, brachytherapy seeds or seed delivery catheters, ultrasound probes, fiber scopes, guidewires, and fiducials or fiducial delivery catheters. Additionally, the lumen may be used to deliver medicine and drugs or to deliver and suction saline for bronchi-aveolar lavage.

In any case, a Doppler catheter is useful to determine whether a blood vessel is present or absent in the area of tissue from which a core sample is desired. As shown, the coring device 150 can be withdrawn so that the coring tip is recessed within the sheath 204 of the sheath device 200. The Doppler catheter 260 is freely advancable through the coring device 150 and can extend from a distal opening of the sheath 204. The proximal end of the Doppler catheter extends back through the coring device 150 and can be coupled to a Doppler processing unit 262 that can provide audio and/or visual feedback to the user. This configuration permits scanning of tissue directly adjacent to the sheath 204 so that the coring device 150 can obtain a core sample of tissue from an area of tissue that was directly examined using the Doppler catheter. Such Doppler catheters can be obtained from Escalon Vascular Access Inc., New Berlin, Wis. In addition, Doppler catheters are described in U.S. Pat. Nos. 6,749,606 issued Jun. 15, 2004; 7,022,088 issued Apr. 4, 2006; 7,422,563 issued Sep. 9, 2008; and 7,393,330 Jul. 1, 2008; U.S. Publication Nos.: US-2003-0130657-A1 filed Oct. 25, 2002; US-2005-0107783-A1 filed Dec. 17, 2004; US-2007-0255304-A1 filed Nov. 22, 2006. The entirety of each of which is incorporated by reference.

Figure 5B:
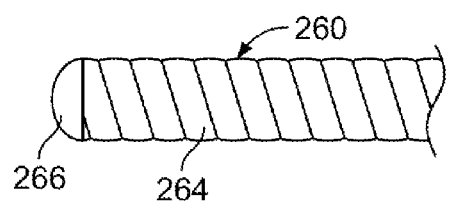
FIG. 5B shows a distal end of the Doppler catheter of FIG. 5A.

FIG. 5B shows a distal end of a variation of a Doppler catheter of FIG. 5A. In this variation, the shaft of the Doppler catheter 260 can comprise a ribbon or wire 264 wound or reinforced structure. The ribbon/wire 264 structure provides sufficient flexibility and column strength so that the Doppler tip 266 can be advanced against tissue that is to be scanned.

Furthermore, in certain variations, the Doppler tip 266 can comprise a transducer or lens in acoustical communication with a transducer that transmits the Doppler signal in a direction parallel or essentially parallel to an axis of the Doppler catheter 260 (and therefore parallel to an axis of the coring device). Such a forward scanning design permits scanning of tissue and structures directly within an intended path of the coring device. Other examples of ultrasound catheters that may be delivered through the needle coring device are endobronchial ultrasound (EBUS) catheters which allow direct visualization of structures below the surface of the airway wall.

Figure 6A:
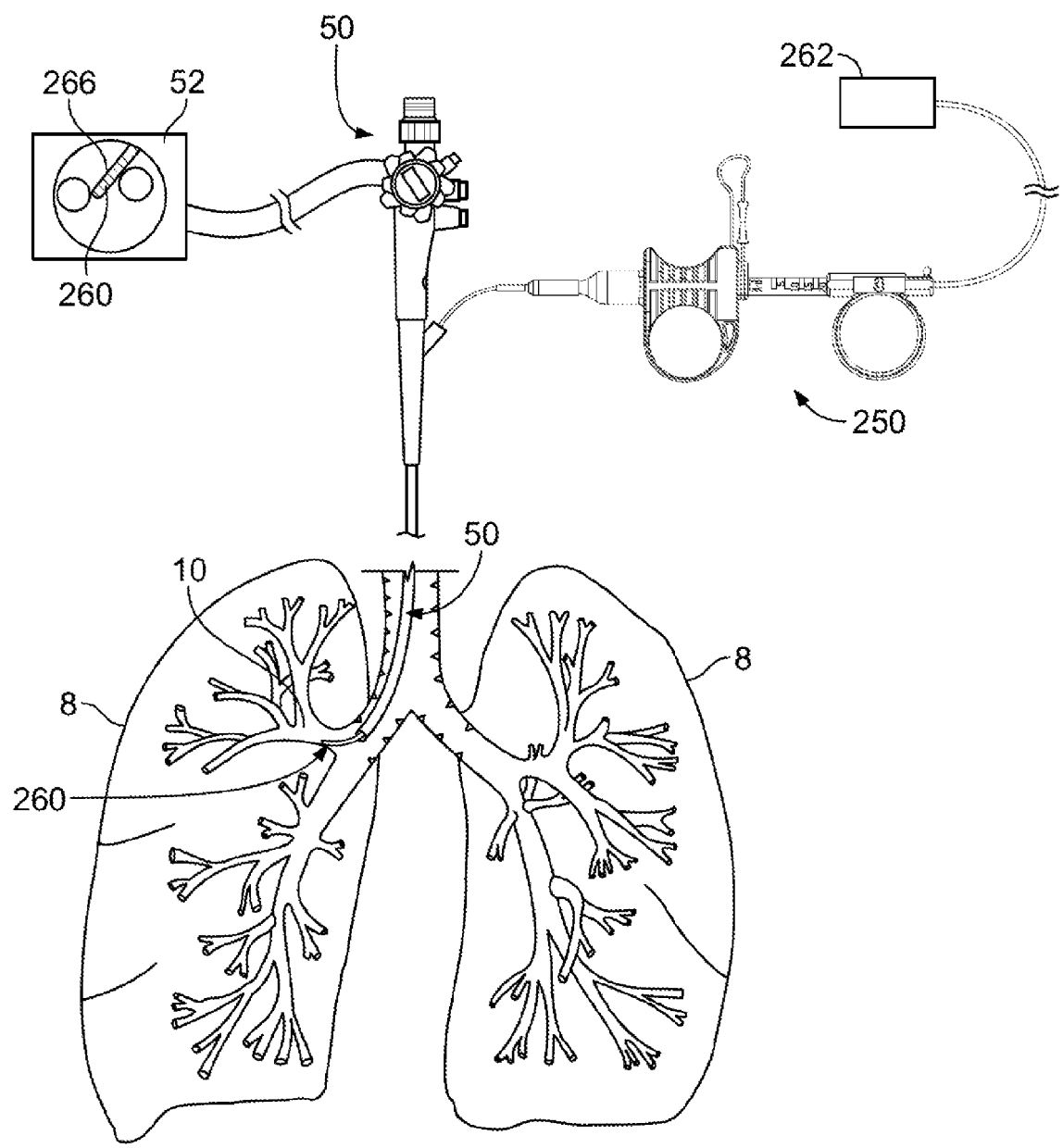
FIG. 6A illustrates the tissue sampling system being advanced through a scope and into lungs of a patient.

FIG. 6A illustrates one example of a tissue sampling system 250 used to obtain a sample of tissue from a remote site within the airways of the lungs. As noted above, the tissue sampling system 250 can be used in a number of regions of the body where the target site is accessed through tortuous anatomy.

As shown in FIG. 6A, the tissue sampling device can be advanced through a scope-type device 50 such as an endoscope (or a bronchoscope when used in the lungs). The scope 50 can include an eyepiece or be coupled to a monitor 52 to allow a physician to remotely observe the target site. In this variation, a physician can advance the scope 50 within the vicinity of (or to) the target region of tissue. Once the scope 50 is in place, a tissue sampling device 100 is inserted through a working channel of the scope 50 so that the distal end of the device 100 is observable through the scope 50 or via the monitor 52. In this example, a Doppler or EBUS catheter 260 is advanced from the tissue sampling device 100 and scope 50 so that the physician can observe the Doppler tip 266 being advanced against tissue to ensure proper scanning of the region. Due to the tidal motion of the tissue, the scanning of tissue can include scanning of the target site as well as scanning of adjacent regions to ensure that no blood vessel (or other structure) is close to create the risk of puncturing of the vessel. The physician can scan to determine the presence or absence of a blood vessel. For example, the physician can use the Doppler device to confirm the presence of a blood vessel beneath the tissue so that a region of tissue can be chosen away from the vessel or that a particular structure to be sampled is below the airway surface so that the physician can accurately target that site. Alternatively, or in combination, the physician can scan the site to confirm that a blood vessel is not within the range of the Doppler catheter, where the Doppler's range scanning range is pre-selected to cover the maximum stroke of the coring device from the sheath. Moreover, the tissue sampling device 100 of the present disclosure can be used with a basic introducer catheter or sheath and without any scope type device.

Once the physician identifies an acceptable site, the Doppler or EBUS can be advanced against tissue so that the tissue sampling device 100 can be placed against that region of tissue. This eliminates the need to reposition the device and risk that the device is placed over a different region of tissue. After the tissue sampling device 100 is in place, the Doppler catheter 260 can be withdrawn through the proximal end of the tissue sampling device 100.

FIGS. 6B to 6C represents both the tissue sampling device 100 located outside of the body of the patient as well as a detailed view of the distal end of the device 100.

FIG. 6B illustrates a state of the device 100 where the Doppler or EBUS probe is removed from the tissue sampling device 100 and the sheath 204 is placed adjacent to the airway tissue 10. As seen on the tissue sampling device 100, the physician moves the adjustable stop 214 from the retracted coring position 184 to the desired location (typically using the incremental markings or depth indicators 182). As discussed herein, this adjustment sets the maximum depth that the core device 150 extends from the sheath device 200.

FIG. 6C illustrates a state of the tissue sampling device 100 where the core device 150 is rapidly advanced relative to the sheath device 200. As noted above, the configuration of the handle or hubs on the core device 150 and sheath device 200 allow for the cannula 158 of the core device 150 to move in a manner similar to that of a biopsy gun. The handles allow for the biomechanics of the physician's/assistants' hand to move the core device 150 and cannula 158 at velocity significantly greater than that possible with a single hand thrust of the device with an extended needle (current common practice). The increased velocity improves the ability of the core tip 156 and cannula 158 to penetrate into tissue to obtain a core sample 12. The ergonomic design of the handle allows for a physician/assistant to use a single hand (freeing the other hand for manipulation of the scope, attaching vacuum to the device, or other equipment). Typically, the operator such as the physician assistant or in some instances, the physician, places an index and middle finger on the sheath handle and a thumb in the core-handle. The movement of these digits together (or the thumb towards the index and middle finger) produces the mechanical advantage and drives the core device 150 forward (the reduced frictional interface between the core shaft and sheath also assist in actuation of the device). Obtaining a core sample in such a manner has been shown in the laboratory to produce a better yield than tissues obtained with standard biopsy devices, namely, TBNA type needles. In some variations, the diameter of the cannula ranged from 18 to 21 Gauge and allow for core sample sizes ranging from 1 to 20 mm. However, variations of the device can include alternative ranges.

As illustrated in FIG. 6D, although the core sample 12 resides within a lumen 162 of the core device 150, the sample 12 may still be attached to tissue at the site. A variation of the system 250 includes the use of a lockable or standard syringe 280 that can be coupled to a proximal end of the core device 150 such that a chamber 284 of the syringe 280 is in fluid communication with a lumen 162 of the core device 150. A stop-cock 286 can fluidly isolate the chamber 284 of the locking syringe 280 such that when a plunger 282 in the syringe 280 is drawn back, a vacuum or negative pressure forms in the chamber 284. Clearly, the order of attachment of the syringe 280 to the core device 150 and/or the drawing of a vacuum can occur in any logical order in addition to that described herein.

Once a vacuum builds in the chamber 284 of the syringe 280, the plunger 282 is locked or held in place to maintain the negative pressure. The stop-cock 286 can fluidly couple the chamber 284 of the syringe 280 to the lumen 162 of the core device 150. As a result, the negative pressure in the chamber 284 draws a vacuum through the core device 150 and effectively separates or grabs the tissue sample 12 from the site. The physician can then remove the tissue sampling device 100 along with the tissue sample 12 from the body.

Although the variation of the system 250 described above relies on a lockable syringe 280 to generate a vacuum, any vacuum source can be used. However, a syringe also permits flushing of the system 250 to expel the sample 12 from the coring device 150. Accordingly, variations of the system can be sold in a kit configuration, where the kit can include any combination of the following components: a tissue sampling device as shown herein; a Doppler or other sensing device; a Doppler processing unit or monitor, a locking syringe; a stopcock; and instructions for use of the system to obtain a tissue core sample.

FIG. 6e shows a stylet 310 for use with the tissue sampling device. The stylet 310 includes a proximal stylet hub 312, an elongate shaft 320 a tube 323, and a distal stylet tip 322. Suitable stylet materials for the shaft include without limitation nitinol and stainless steel. Suitable materials for the tube 323 include without limitation nylon, polyethylene, PEBAX, polyurethane, Nitinol, and other flexible materials.

FIG. 6f shows the stylet 310 advanced through the coring device 340. The stylet is advanced until stylet hub 312 makes contact with a corresponding mating connector on the coring device 340. Examples of connectors include luer lock connectors. Once positioned in the coring device 340, and locked in place, the stylet is adapted to move in registration with the coring device needle 344.

In another embodiment, stylet hub 312 and the mating connector of the coring device 340 cooperatively engage to controllably advance the stylet relative to the needle. In one example, cooperative structures are threads that allow an operator to advance the stylet relative to the needle in increments. Another example is to employ detents to allow incrementing the stylet forward in a controlled manner.

The presence of the stylet in the tissue sampling device serves to make the shaft of the tissue sampling device stiffer. This is advantageous for penetrating relatively tough or stiff tissues such as, for example, the upper bronchial airway or tracheal wall.

However, different locations within the human lungs may require different levels of device stiffness. As a result, the present invention may include a suite of stylets with varying stiffnesses and flexibilities. For example, the user may decide to use the tissue sampling device without a stylet for locations deep in the periphery where great flexibility is required but significant stiffness is not. Alternatively, for a location in the proximal lung, near the main carina where the airway wall is toughest due to the presence of significant cartilage rings and tough tissue in between, the user may select the stiffest stylet with the least flexibility (assuming tight radiused bends are not required to access the target location) to provide the highest likelihood for penetrating the airway wall. Varying stylet stiffnesses is accomplished by varying the diameter and material properties of the stylet shaft. For stylet shafts smaller in diameter than the needle bore, a polymer tube 323 may be fitted around the stylet shaft to maintain a smooth fit between the stylet assembly and the needle bore. The polymer tube material will influence the stiffness and flexibility balance so different polymer materials are likely to be used for different stylet assemblies. The combination of stylet diameter and material plus the polymer material will be integrated to produce a variety of different stylet assemblies. For example, stylet shafts may range from 0.015" to 0.038" for a 18 gage needle. For a 21 gage needle, stylet shaft sizes may range from 0.010" to 0.020". In these embodiments, as the stylet shaft diameter decreases from the maximum value, a polymer sleeve will be added to minimize the gap between the needle bore and the stylet assembly. Using this approach, numerous combinations of stylet diameters and polymer sleeves may be combined into different stylet assemblies to provide a great variety of tissue sampler stiffness and flexibility solutions.

After the desired tissue penetration has been achieved through a tissue (e.g., airway wall), and a clear pathway to the target to be sampled exists, the stylet is removed from the coring device. A histology core may be obtained as described above including the option of adjusting the depth stop 350, and applying vacuum or suction to facilitate collection of a core sample from the target. Examples of target tissues include without limitation lymph nodes, lesions, or tumors.

In another embodiment of the present invention, the tissue sampling device includes a means to vary or adjust its stiffness. The stiffness of the device is adjusted by positioning one of a plurality of stylets in the shaft. Each stylet has a different flexibility ranging from flexible to stiff. A difference in stylet flexibility may arise from a number of stylet properties including material, size, shape, coatings, and manufacturing techniques. At the user's discretion, a first stylet is selected having a first flexibility and is positioned within the coring needle to provide a first stiffness. In this manner, or by replacing the first stylet with a second stylet, the stiffness of the coring device is adjusted. Additionally, removal of the stylet increases the shaft flexibility. Consequently, this embodiment of the present invention provides a means to, selectively vary or adjust the flexibility of the tissue sampling device. Another use of the stylet is to mechanically eject a core sample from the lumen of the needle.

Figure 7:
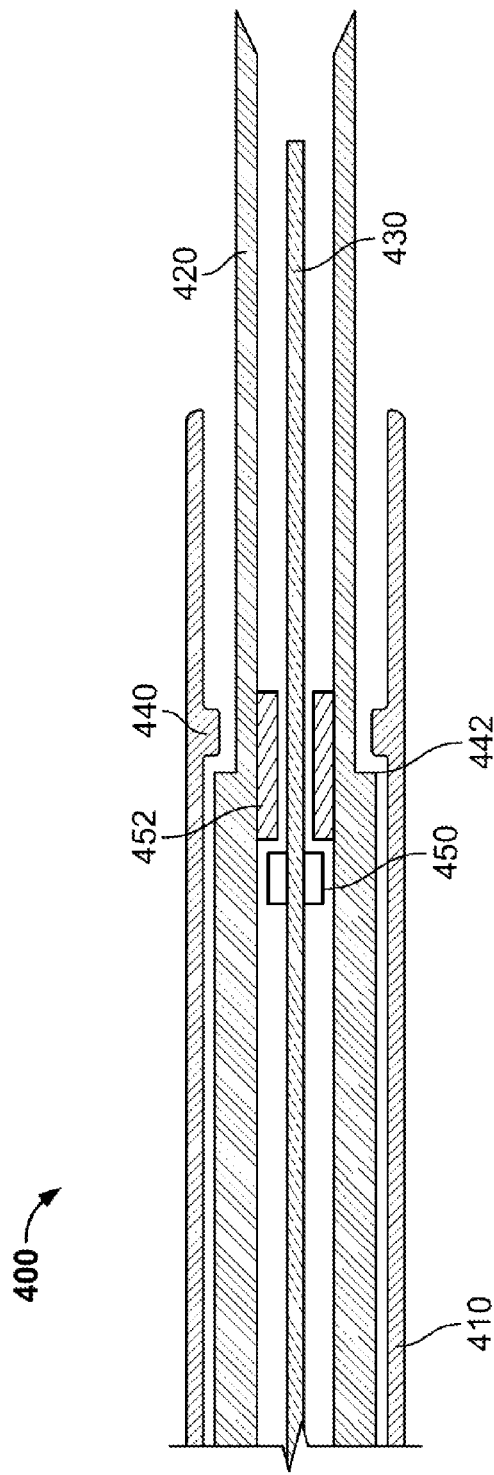
FIG. 7 illustrates another tissue sampling system including a sheath, needle and stylet and cooperating stop features.

FIG. 7 illustrates another tissue sampling device 400 including a sheath 410, needle 420, and stylet 430. The sheath 410 is shown including a sheath flat 440. Once needle collar 442 of the needle contacts the sheath flat, the needle is prohibited from further advancement relative to the sheath. In an application, the needle and sheath may be advanced together and the rigidity of tissue sampling device is increased by the presence of the sheath. This is desirable in certain applications where increased rigidity is needed such as, for example, penetration of the larger airways.

The rigidity may be further increased by the presence of stylet 430. With reference to FIG. 7, stylet 430 is shown having a stylet collar 450 which prohibits stylet from advancing distally beyond needle flat 452. The stylet is advanced though the needle until stylet collar contacts the needle flat 452. The end of the stylet preferably extends to the needle opening and preferably not beyond the needle opening. The components then move together such that the rigidity of the tissue sampling device is increased.

Additionally, the stylet serves to prevent sampling of undesirable tissue such as, for example, the airway wall when the needle is being used to penetrate the airway wall. The stylet may also be used to clear the needle bore and to express a tissue sample.

Additionally, the depth that the needle extends from the sheath, and the depth that the stylet extends relative to the needle, are controlled with the above described collars and flats. The maximum distances are predetermined. In one embodiment, the maximum distance that the needle extends from the sheath ranges from 5 to 40 mm, and more preferably from 15 to 25 mm. The flats, collars and stops may be made in a wide variety of ways. For example, a flat or collar may be made using polymer or metal tubing, or a coil. The components may be bonded to the associated member by welding or adhesives.

Figure 8:
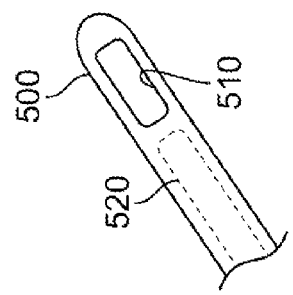
FIG. 8 illustrates a partial view of another tissue sampling device including a sheath having a lateral opening.

Additionally, in another embodiment of the present invention, and with reference to FIG. 8, sheath 500 may comprise a lateral or side window 510 or port which can be used with any of the shafts 520 or cannula tips described above. The side window 510 is used in conjunction with suction to allow the user to draw tissue into the sheath, and then the cannula tip is driven forward to excise a core or sample. This facilitates obtaining samples from the side of the instrument when articulation may be difficult.

In another embodiment of the present invention the tissue sampling device includes steering functionality. A pull wire extends along the sheath and is actuated to turn the sheath in a direction. The needle is then advanced from the sheath at the desired angle.

In another embodiment of the present invention, the tissue sampling device includes a guide wire lumen in addition to the working channel or lumen for the needle. The guidewire lumen may be coaxially disposed relative to the needle lumen. The guidewire is advanced first to a target location or position and the tissue sampling device is advanced along the guidewire into the proper position. The guidewire itself is preferably radiopaque. Nitonol is an example material for the guidewire. The guidewire may additionally be equipped with an anchoring tip such that the guidewire may be actuated to anchor itself to a target site. To this end, a hook or balloon may be present at the tip of the guidewire to hold it to a tissue structure.

In another embodiment of the present invention, the outside of the sheath of the coring needle may be marked with any pattern of symbols, lines, or marks to help visualize the sheath.

In the above explanation of Figures similar numerals may represent similar features for the different variations of the invention.

The invention herein is described by examples and a desired way of practicing the invention is described. However, the invention as claimed herein is not limited to that specific description in any manner. Equivalence to the description as hereinafter claimed is considered to be within the scope of protection of this patent.

The devices of the present invention are configured to obtain a core sample of tissue or a sample of tissue from a target site within a body of a patient. Although the device is discussed as being primarily used in the lungs, the device is not limited as such and it is contemplated that the invention has utility in other areas as well, specifically in applications in which blood vessels or other structures must be avoided while cutting or removing tissue.

The above illustrations are examples of the invention described herein. It is contemplated that combinations of aspects of specific embodiments/variations or combinations of the specific embodiments/variations themselves are within the scope of this disclosure.

We claim:

1. A tissue sampling device, configured to have multiple set penetration depths, the device comprising:
   a sheath being flexible to advance through tortuous anatomy;
   a shaft extending in the sheath, wherein the shaft has a lumen and where the shaft and sheath are moveable relative to each other;
   a coring tip located at a distal end of the shaft, the coring tip having a tissue penetrating distal end and an axially disposed cavity to excise a tissue sample as the coring tip is advanced axially;
   a handle assembly comprising a sheath hub and a coring hub moveably coupled thereto, the sheath hub located on the sheath and the coring hub located on the shaft, where the sheath hub and coring hub each include a grip surface located on the respective hubs to allow for a single handed movement of the coring hub relative to the sheath hub for moving the shaft relative to the sheath and driving the coring tip forward wherein the forward driving of the coring tip can cut a tissue sample and capture the cut tissue sample in the cavity of the coring tip, where a length of the shaft and coring hub relative to a length of the sheath and the sheath hub is selected such that when the sheath hub is spaced a maximum distance from the coring hub, the coring tip is located within the sheath and when the sheath hub is spaced a minimum distance from the coring hub, the coring tip advances from the sheath; and the coring hub further comprising at least a plurality of recesses each configured to removably nest a stop member, the plurality of recesses being located along a length of the coring hub, such that when the stop member is in one of the recesses, the stop member limits an advancement distance that the coring tip advances from the sheath.

2. The tissue sampling device of claim 1, further comprising at least one distance indicator associated with at least one recess, where the indicator provides visual confirmation of the penetration depth of the device.

3. The tissue sampling device of claim 1, where the sheath includes a reinforcing coil in at least a portion of the sheath.

4. The tissue sampling device of claim 1, where the shaft comprises a coil extending along at least a portion of the shaft.

5. The tissue sampling device of claim 1, where the coring device comprises a lumen that extends from the coring tip through a rear surface of the coring hub.

6. The tissue sampling device of claim 1, where the coring tip comprises a cannula having a sharpened distal end.

7. A method of obtaining a tissue sample from an airway in a lung by pre-selecting a maximum depth of the sample in tissue, the method comprising:

advancing a tissue sampling catheter into an airway of the lung, where the tissue sampling catheter comprises a sheath having a shaft extending therethrough, the shaft having a coring tip comprising a tissue penetrating distal end to penetrate tissue and a cavity to excise the tissue sample, where the coring tip is retracted within the sheath when the tissue sampling catheter enters the airway of the lung;

positioning a distal end of the sheath adjacent to a site in the airway;

setting an adjustable stop on a handle of the tissue sampling catheter, where a location of the adjustable stop on the handle determines a pre-determined distance that the coring tip extends from the sheath, where the pre-determined distance corresponds to the maximum depth;

actuating the handle to extend the coring tip from the sheath by the pre-determined distance thereby penetrating tissue with the coring tip such that the sample of tissue is located within the cavity of the coring tip.

8. The method of claim 7, where penetrating tissue with the coring tip comprises actuating the handle to drive the coring tip to penetrate tissue, where the handle comprises a sheath hub and a coring hub moveably coupled thereto, where the sheath hub and coring hub each include a digit grip surface located on the respective hubs to allow for single handed movement of the coring hub relative to the sheath hub by the pre-determined distance for moving the sheath relative to the shaft.

9. The method of claim 7, wherein said shaft further comprises a contiguous lumen to hold multiple samples of tissue, and further comprising obtaining multiple samples of tissue from multiple penetration sites.

10. The method of claim 7, wherein advancing a tissue sampling catheter into an airway of the lung, comprises advancing the tissue sampling catheter through tortuous anatomy to access the tissue sample.

* * * * *